(12) United States Patent
McGinley et al.

(10) Patent No.: US 9,480,571 B2
(45) Date of Patent: Nov. 1, 2016

(54) ANKLE REPLACEMENT SYSTEM AND METHOD

(71) Applicant: Wright Medical Technology, Inc., Arlington, TN (US)

(72) Inventors: Shawn E. McGinley, Arlington, TN (US); Braham K. Dhillon, Memphis, TN (US); Ramon Luna, Arlington, TN (US); Robert M. Howles, Bartlett, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 331 days.

(21) Appl. No.: 14/100,799

(22) Filed: Dec. 9, 2013

(65) Prior Publication Data

US 2014/0188236 A1    Jul. 3, 2014

Related U.S. Application Data

(60) Provisional application No. 61/746,393, filed on Dec. 27, 2012.

(51) Int. Cl.
*A61F 2/42* (2006.01)
*A61F 2/46* (2006.01)
*A61B 17/15* (2006.01)
(Continued)

(52) U.S. Cl.
CPC ............ *A61F 2/4202* (2013.01); *A61B 17/15* (2013.01); *A61B 17/1682* (2013.01); *A61F 2/4684* (2013.01); *A61B 2017/1775* (2013.01); *A61F 2002/4205* (2013.01)

(58) Field of Classification Search
CPC .................. A61B 17/1682; A61B 2017/1775; A61F 2002/4205; A61F 2/4684
See application file for complete search history.

(56) References Cited

U.S. PATENT DOCUMENTS

| 3,872,519 A | 3/1975 | Giannestras et al. |
| 3,889,300 A | 6/1975 | Smith |

(Continued)

FOREIGN PATENT DOCUMENTS

| WO | 2006/023824 A2 | 3/2006 |
| WO | 2006/099270 A2 | 9/2006 |

(Continued)

OTHER PUBLICATIONS

International Search Report for PCT/US2014/027448 dated Jul. 2, 2014.

(Continued)

*Primary Examiner* — Andrew Yang
(74) *Attorney, Agent, or Firm* — Duane Morris LLP

(57) ABSTRACT

A position adjustment device having a tool holder is locked to at least two pins projecting from respective anterior facing locations near a distal end of a tibia of a patient. The position adjustment device is adjusted. The position adjustment device is locked with the tool holder at first coordinates in the proximal-distal and medial-lateral directions. The distal end of the tibia is resectioned with a tool positioned on the tool holder, while the tool holder is in the first coordinates in the proximal-distal and medial-lateral directions. The tool is removed from the tool holder. A tibia trial is placed on the resectioned tibia using the tool holder, while the tool holder is in the first coordinates in the proximal-distal and medial-lateral directions. The tibia trial has a size and shape of a tibial tray of an ankle replacement system.

4 Claims, 17 Drawing Sheets

(51) Int. Cl.
*A61B 17/16* (2006.01)
*A61B 17/17* (2006.01)

(56) References Cited

U.S. PATENT DOCUMENTS

| | | | |
|---|---|---|---|
| 5,312,412 A | 5/1994 | Whipple | |
| 5,354,300 A | 10/1994 | Goble et al. | |
| 5,776,200 A | 7/1998 | Johnson et al. | |
| 6,342,056 B1 | 1/2002 | Mac-Thiong et al. | |
| 6,620,168 B1 | 9/2003 | Lombardo et al. | |
| 6,645,215 B1 | 11/2003 | McGovern et al. | |
| 6,942,670 B2 | 9/2005 | Heldreth et al. | |
| 7,001,394 B2 | 2/2006 | Gundlapalli et al. | |
| 7,534,246 B2 | 5/2009 | Reiley et al. | |
| 7,850,698 B2 | 12/2010 | Straszheim-Morley et al. | |
| 8,002,841 B2 * | 8/2011 | Hasselman | A61B 17/15 623/21.18 |
| 8,034,114 B2 | 10/2011 | Reiley | |
| 8,048,164 B2 | 11/2011 | Reiley | |
| 8,114,091 B2 | 2/2012 | Ratron et al. | |
| 8,313,492 B2 | 11/2012 | Wong et al. | |
| 8,475,463 B2 | 7/2013 | Lian | |
| 8,808,303 B2 * | 8/2014 | Stemniski | A61B 17/15 606/96 |
| 2002/0082607 A1 | 6/2002 | Heldreth et al. | |
| 2004/0030399 A1 | 2/2004 | Asencio | |
| 2006/0247788 A1 | 11/2006 | Ross | |
| 2007/0276400 A1 | 11/2007 | Moore et al. | |
| 2009/0105767 A1 | 4/2009 | Reiley | |
| 2010/0305572 A1 | 12/2010 | Saltzman et al. | |
| 2012/0277745 A1 * | 11/2012 | Lizee | G01B 5/24 606/59 |
| 2013/0116797 A1 * | 5/2013 | Coulange | A61B 17/15 623/21.18 |

FOREIGN PATENT DOCUMENTS

| | | |
|---|---|---|
| WO | WO 2007/084846 | 7/2007 |
| WO | WO 2009/158522 | 12/2009 |
| WO | WO 2011/151657 | 12/2011 |

OTHER PUBLICATIONS

Search report for EP 13198280 dated Feb. 5, 2014.
International Preliminary Report on Patentability issued by the International Bureau of WIPO in connection with International patent application No. PCT/US2014/027448, Sep. 15, 2015, 8 pages.

* cited by examiner

ANKLE REPLACEMENT SYSTEM AND METHOD

FIELD

This application is a non-provisional of U.S. Patent Application No. 61/746,393, which was filed Dec. 27, 2012, the entirety of which is incorporated by reference herein.

This disclosure relates to prosthetics generally, and more specifically to systems and methods for total ankle replacement.

BACKGROUND

The ankle is a joint that acts much like a hinge. The joint is formed by the union of three bones. The ankle bone is the talus. The top of the talus fits inside a socket that is formed by the lower end of the tibia, and the fibula, the small bone of the lower leg. Arthritis, bone degeneration and/or injury can cause ankle joint deterioration resulting in pain, reduced range of motion, and decreased quality of life. In many cases, physicians are recommending ankle replacement surgery with an implant as an option.

Available ankle replacement systems include, for example, the "INBONE"™ system sold by Wright Medical Technologies of Arlington, Tenn. The "INBONE"™ system includes a talar tray component with stem, which fit into a resectioned distal end of the tibia. A poly insert having a concave distal surface is joined to the tibial tray. A talar dome and stem are implanted in a resectioned proximal end of the talus. The poly insert is configured to articulate with the talar dome.

Associated tools enable the physician to immobilize the foot, while the physician performs appropriate drilling and resectioning of the bones, and implants the prosthetic ankle. An example of such a tool is described in U.S. Pat. No. 7,534,246.

Improved devices and methods are desired.

SUMMARY

In some embodiments, a position adjustment device having a tool holder is locked to at least two pins projecting from respective anterior facing locations near a distal end of a tibia of a patient. The position adjustment device is adjusted. The position adjustment device is locked with the tool holder at first coordinates in the proximal-distal and medial-lateral directions. The distal end of the tibia is resectioned with a tool positioned on the tool holder, while the tool holder is in the first coordinates in the proximal-distal and medial-lateral directions. The tool is removed from the tool holder. A tibia trial is placed on the resectioned tibia using the tool holder, while the tool holder is in the first coordinates in the proximal-distal and medial-lateral directions. The tibia trial has a size and shape of a tibial tray of an ankle replacement system.

DETAILED DESCRIPTION

Figure 1:
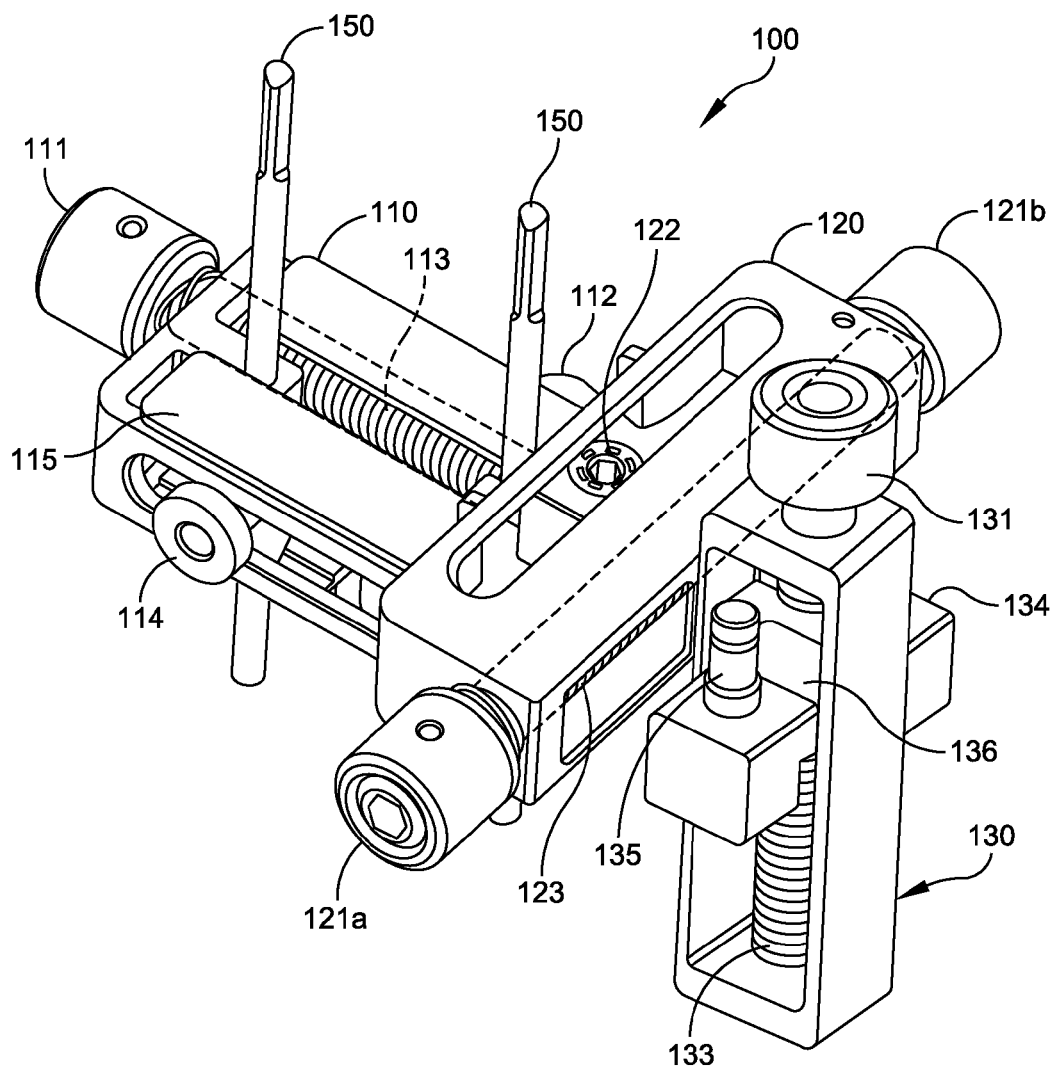
FIG. 1 is an isometric view of a position adjustment device, or adjustment block suitable for sizing and trialing an implant.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIG. 1 is an isometric diagram of a position adjustment device 100 (also referred to below as an "adjustment block") for positioning of drilling and cutting tools for tibia resectioning, and for tibia trial insertion. The adjustment block 100 provides a common reference location for locating tools and the tibia trial components throughout the sizing, resectioning and trial procedure. In some embodiments, the adjustment block 100 is small enough in profile to position a cut guide into the wound space close to the tibia bone without applying excess skin tension. The physician can use the adjustment block to position a drill guide and/or cut guide closer to the tibia bone, to make more accurate cuts with less chance of the blade or pins flexing.

The adjustment block 100 has three independently positionable frames 110, 120, and 130 for precisely positioning a tool holder 134 adjacent the joint to be replaced.

The first frame 110 is configured to be attached to two fixation pins 150 which have been inserted in the anterior surface of the tibia, near the distal end of the tibia. A locking screw 112 actuates a locking plate (not shown), which bears against the fixation pins 150 to secure the adjustment block 100 relative to the pins. The first frame has a proximal-distal adjustment knob 111 coaxially connected to a screw 113. The screw 113 can have an Acme thread, trapezoidal thread, square thread or other suitable thread for leadscrew use. The second frame 120 is fixedly attached or unitarily formed with a leadscrew nut (not shown), which the screw 113 drives. Rotation of the proximal-distal adjustment knob 111 rotates screw 113 to advance or retract the second frame 120 in the proximal-distal direction. When the second frame 120 is at the desired proximal-distal coordinate, the physician advances the locking screw 114 to lock the second frame 120 to the first frame 110 in place.

The second frame 120 has at least one medial-lateral adjustment knob 121a, 121b coaxially connected to a screw 123. The screw 123 can have an Acme thread, trapezoidal thread, square thread or other suitable thread for leadscrew use. The screw 123 drives a leadscrew nut (not shown), to which the third frame 130 is fixedly attached or unitarily formed with. Rotation of the medial-lateral adjustment knob 121a or 121b rotates screw 123 to move the third frame 130 in the medial-lateral direction. When the third frame 130 is at the desired medial-lateral coordinate, the physician advances the locking screw 122 to lock the leadscrew 123 of the second frame 120 in place.

The third frame 130 has an anterior-posterior adjustment knob 131 coaxially connected to a screw 133. The screw 133 can have an Acme thread, trapezoidal thread, square thread or other suitable thread for leadscrew use. The screw 133 drives a leadscrew nut 136, to which a tool holder 134 is fixedly attached or with which tool holder 134 is unitarily formed. Rotation of the anterior-posterior adjustment knob 131 rotates screw 133 to move the tool holder 134 in the anterior-posterior direction. The tool holder 134 is adapted to hold a drilling tool, a cutting tool, or a tibia trial 210.

Figure 2:
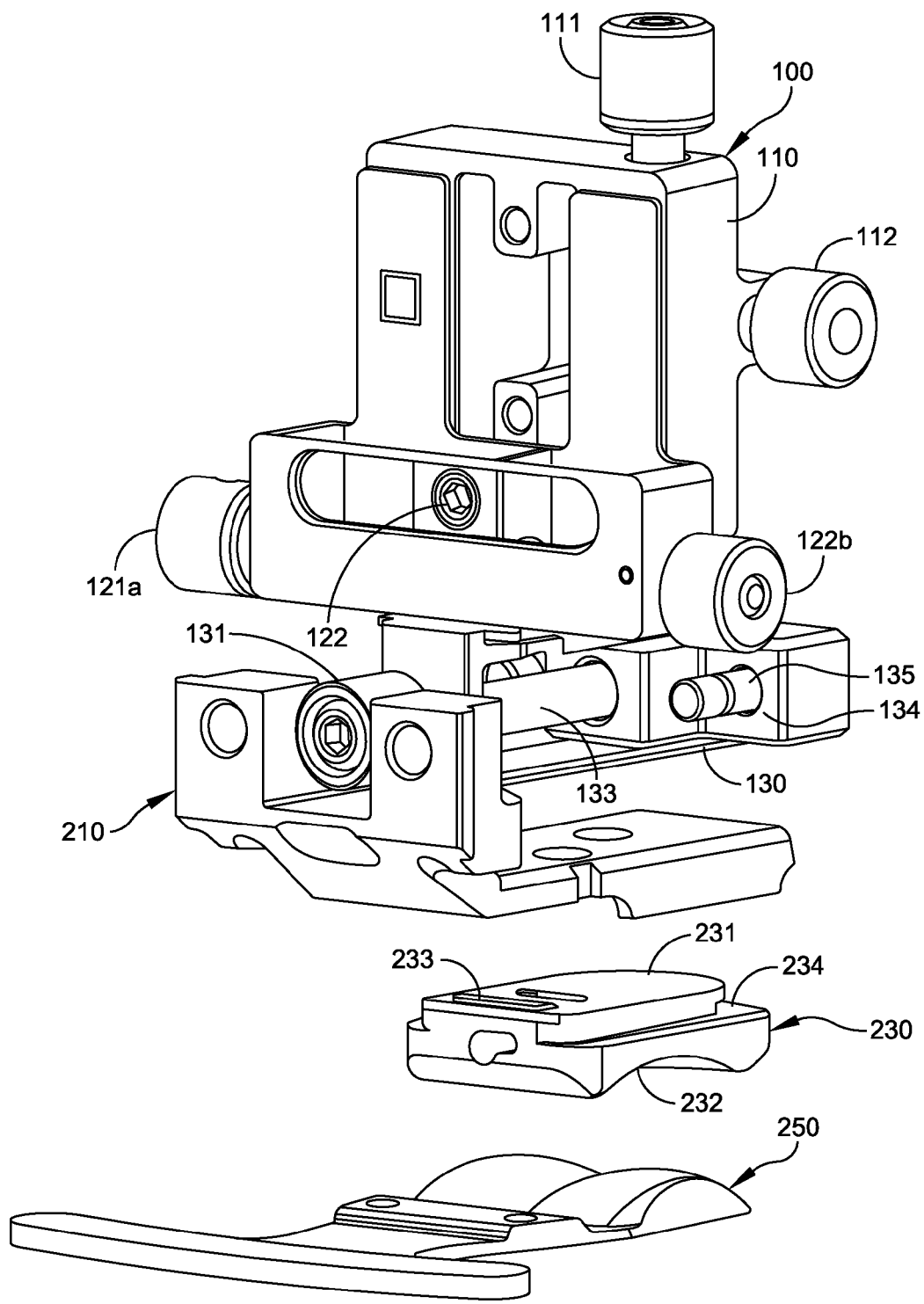
FIG. 2 is an exploded view showing the adjustment block, tibial trial, poly trial insert, and floating trial.
Figure 3:
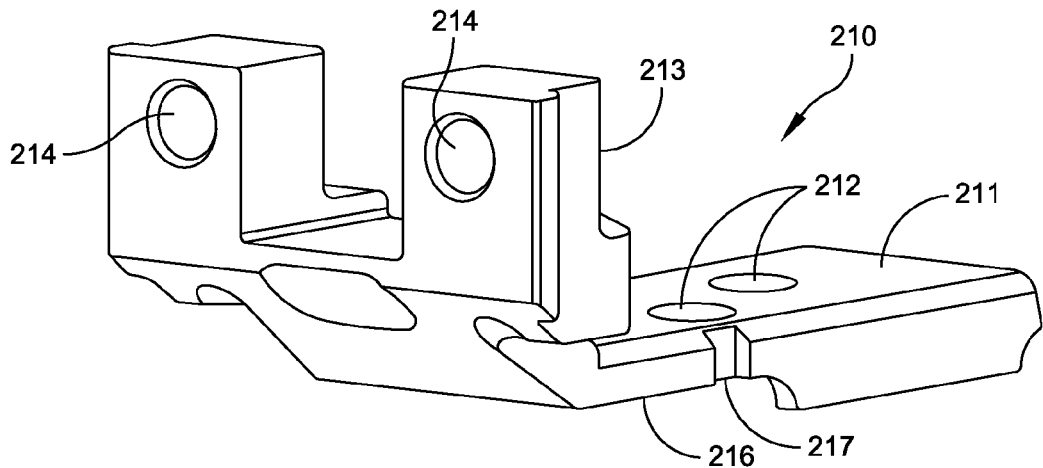
FIG. 3 is an isometric view of the tibia trial of FIG. 2.
Figure 4:
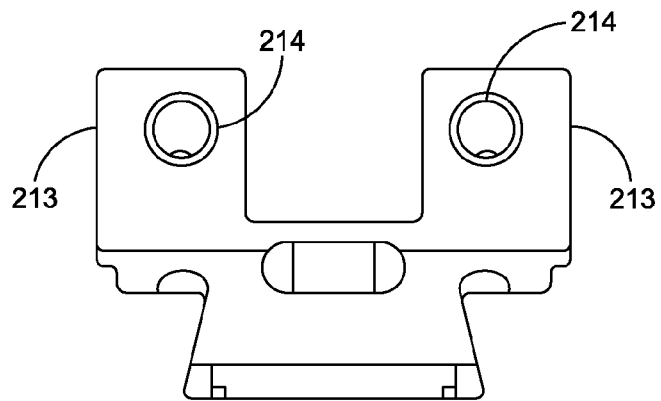
FIG. 4 is an anterior elevation view of the tibia trial of FIG. 3.
Figure 5:
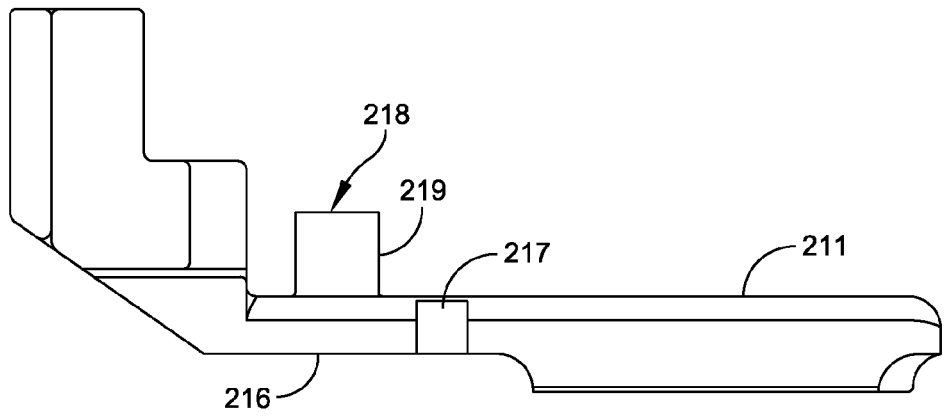
FIG. 5 is a lateral elevation view of the tibia trial of FIG. 3.

FIG. 2 is an exploded view showing the adjustment block 100, tibia trial 210, poly trial insert 230 and floating trial 250. FIG. 3 is an isometric view of the tibia trial 210. FIG. 4 is an anterior (rear) elevation view of the tibia trial 210. FIG. 5 is a sagittal (side) elevation view of the tibia trial 210.

The tibia trial 210 provides the profile of the tibia tray portion of an ankle replacement system. The tibia trial 210 comprises a plate 211 with a top surface adapted to fit against a distal surface 262 of the resectioned tibia 260. The plate 211 has a plurality of holes 212 to be used to locate peg holes 263 in the resectioned tibia 260. The plate 211 has a bottom surface 216 adapted to receive a trial insert, such as a poly trial insert 230. An anterior tibia reference member 218 extends from the plate 211. The anterior tibia reference member 218 has a posterior surface 219 adapted to contact an anterior surface 261 of the tibia 260 when the tibia trial 210 is properly positioned. The tibia trial 210 has an anterior mounting portion 213 sized and shaped to be mounted to the tool holder 134 of the adjustment block 100. In some embodiments, the tibia trial 210 has a notch 217 for aligning an anterior surface of the poly trial insert 230 with the tibia trial 210. Alignment (or misalignment is readily visible by checking whether the notch 217 is aligned with an edge of the poly trial insert 230. In some embodiments, the tibia trial 210 is formed of a strong, corrosion resistant material such as stainless steel or a titanium alloy.

The poly trial insert 230 is configured to provide the profile of the poly insert of an ankle replacement system. The poly trial insert 230 comprises a top surface 231 adapted to be detachably mounted to the bottom surface of the plate 216 of the tibia trial 210. The poly insert 230 has a concave bottom surface 232 with a size and shape of a prosthetic tibia joint surface of the ankle replacement system. The thickness of the poly trial insert 230 matches the poly insert of the ankle replacement system to which the poly trial insert 230 corresponds, allowing verification of the size and thickness of the poly insert using the poly trial insert 230. In some embodiments, the poly insert of the ankle replacement system has a locking tab to prevent release from the talar tray after surgery; but the poly trial insert 230 has a non-locking tab 233 with a ramped surface, to be detachably inserted in the tibia trial 210 and removed after sizing and resectioning is completed. The non-locking tab 233 fits in a corresponding recess (not shown) in the bottom surface 216 of the tibia trial 210. The posterior end of the poly trial insert 230 has an undercut 234, In some embodiments, the poly trial insert 230 is made from the same type of material used in the poly insert of an ankle replacement system. In some embodiments, the poly trial insert 230 is made of a chemical-resistant material such as polyphenylsulfone, which is also referred to as RadelR.

Figure 6:
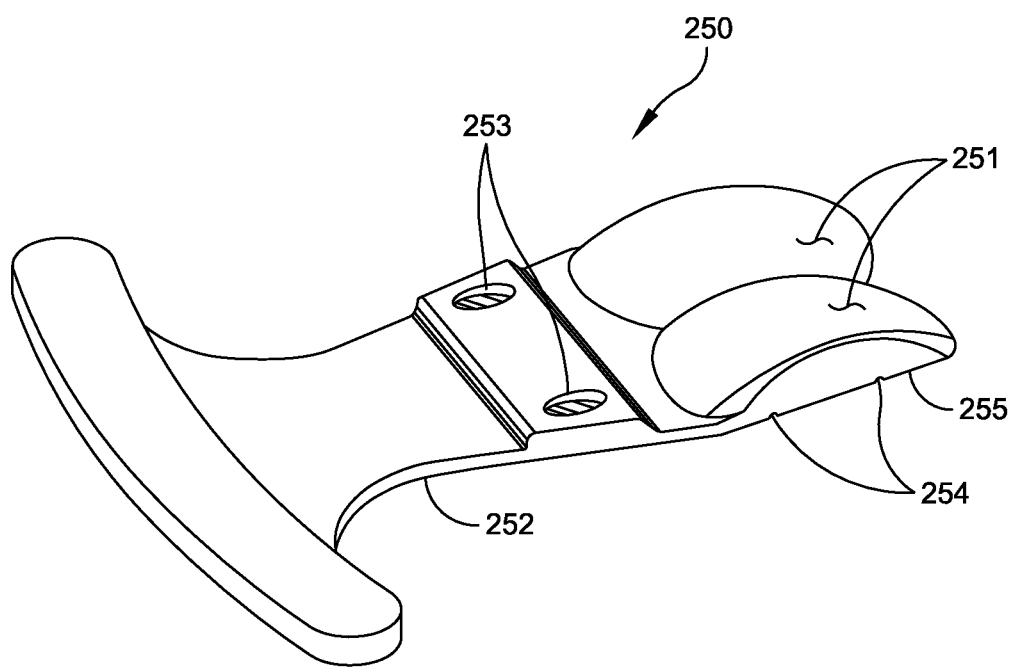
FIG. 6 is an isometric view of the floating trial of FIG. 2.

FIG. 6 is an isometric view of the floating trial 250. The floating trial 250 is configured to provide a contour that matches the contour of the talar dome of the ankle replacement system. The floating trial 250 is configured to be inserted beneath the poly trial insert 230 to contact the concave bottom surface 232 of insert 230. The floating trial 250 comprises a member 251 having at least one convex anterior surface with a size and shape of a prosthetic talar dome of the ankle replacement system, to permit articulation with the concave surface 232 of the insert. The posterior surface 255 of the member 251 is shaped to match the contour of the resectioned talus. In some embodiments, the floating trial 250 has two convex surfaces 251. The floating trial 250 further includes a handle portion 252 which is sized to project from the resection site, so the physician can easily optimize the position of the floating trial for smooth articulation with the poly trial insert 230. The handle 252 of the floating trial 250 has a plurality of pin holes 253 for receiving fixation pins to be used for locating a talar cut guide (not shown). Once the position is optimized, the pins are inserted through the pin holes 253 before completing the resectioning of the talus. In some embodiments, the floating trial 250 is formed of a strong, corrosion resistant material such as stainless steel or a titanium alloy. In some embodiments, the floating trial 250 also has one or more anterior chamfers 254 for reference and alignment.

FIGS. 7-17 show various stages of a method of resectioning and trialing, using the adjustment block 100, optional drill guide 280, optional cut guide 290, tibia trial 210, poly trial insert 230 and floating trial 250. This is one example of a use of the devices, but is not limiting.

Figure 7:
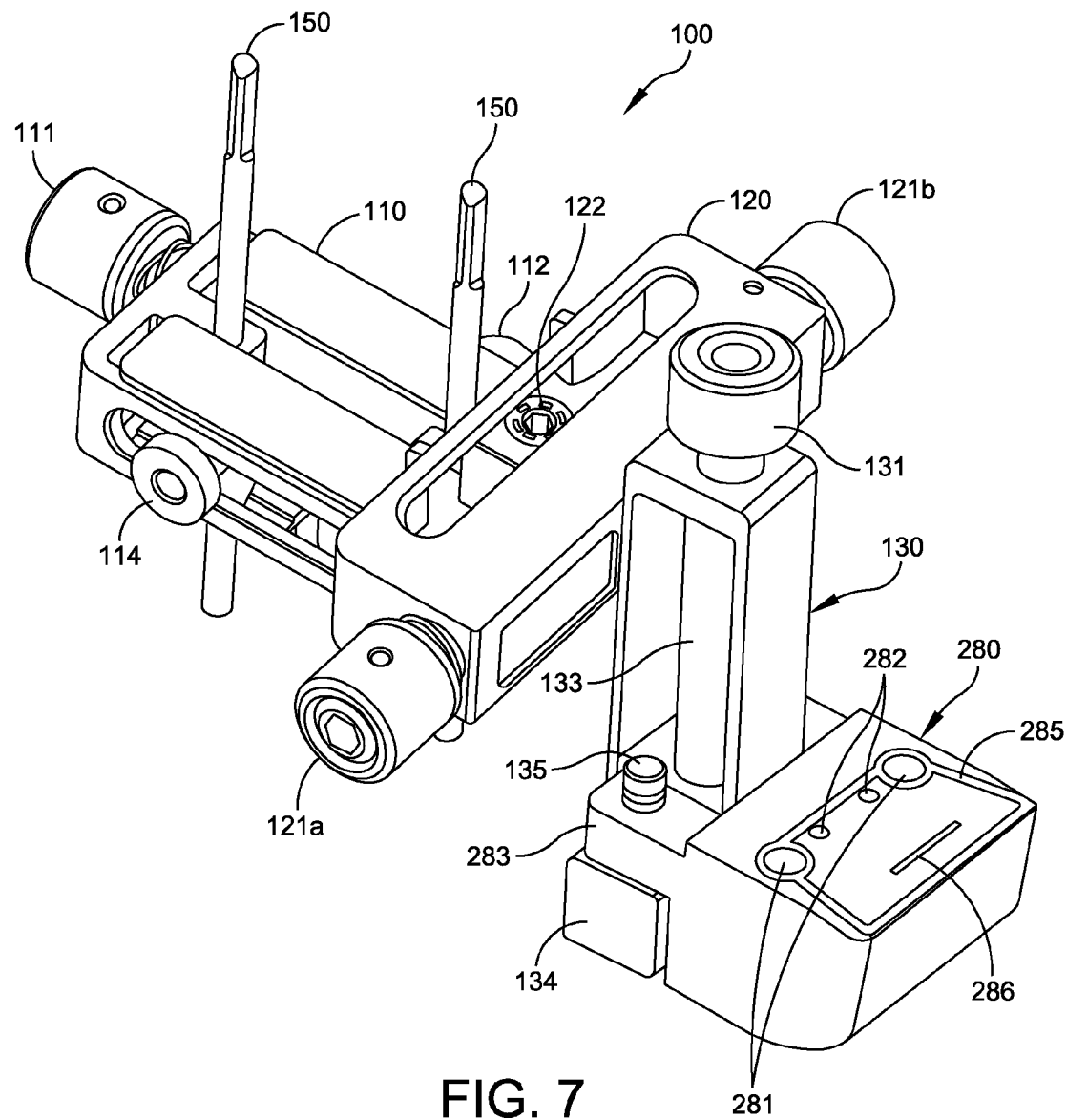
FIG. 7 is an isometric view of an adjustment block of FIG. 1, holding a drilling guide.

FIG. 7 shows the adjustment block 100 fixed to the fixation pins 150 (e.g., 3.2 mm pins) which have been inserted in the anterior surface of the tibia 260 near the distal end 261 of the tibia. FIG. 7 also shows a drill guide 280 attached to the tool holder 134 of the adjustment block 100, with the first frame 110 slightly above the anterior surface of the tibia 260. In some embodiments, the tool holder 134 is stage with a pair of pins 135, and the drill guide 280 has a corresponding pair of mounting ears 283 with holes adapted to snap onto the pins 135. This tool holder design is just exemplary in nature, and other embodiments include other suitable mounting structures.

In the embodiment of FIG. 7, the drill guide 280 is a small profile device sized and shaped to be inserted beneath the refracted skin (not shown) in the ankle region. The drill guide 280 has at least two guide holes 281 to be used to drill pilot holes in the tibia 260. The drill guide also has pin holes 282 that can be used to pin the drill guide to the bone, for position fixation. In some embodiments, the drill guide 280 has sizing patterns 285 showing the size and location of one or more resectioning cuts corresponding to the holes to be drilled using the drill guide 280. In some embodiments, the drill guide 280 has one or more reference lines 286 that the physician can optionally use to position the drill guide 280 (by adjusting the proximal-distal knob 111, the medial-lateral knob 121a or 121b, and the anterior-posterior knob. In some embodiments, the lines 285, 286 are visible under a fluoroscope, so the physician can view the position and size of the lines 285, 286 in situ, relative to the patient's bones.

The physician sizes the tibial tray component of the ankle replacement system by mounting a drill guide 280 on the tool holder and adjusting its position as described above. The position adjustment device (adjustment block) 100 is locked with the tool holder 134 at first coordinates in the proximal-distal and medial-lateral directions.

The physician views the X-ray of the tibia bone 260 and drill guide 280 and determines whether it is the optimum size and position for the patient. The position can be adjusted based on the X-ray, using knobs 111, 121, 131. If the size of the resectioning cut corresponding to the drill guide 280 is too large or too small, the physician removes the drill guide, selects a different size drill guide, and snaps the new drill guide onto the tool holder 134 of the adjustment block 100. The drill guide is then repositioned against the tibia, imaged by fluoroscope, and the size is again checked. To facilitate fluoroscopic X-ray imaging, the drill guide 280 can be made of plastic, while the circles surrounding holes 281 and the patterns 285, 286 can be made of metal. Thus, only the circles surrounding holes 281 and the patterns 285, 286 appear on the X-ray, superimposed against the tibia 260 and talus 265.

Although some embodiments use a single drill guide 280 for sizing, location of fixation pins by holes 282 and drilling corners 281, other embodiments (not shown) use a first guide (sizing guide) with holes 282 and patterns 285, 286 for sizing the tibia trial 210 and locating the fixation pins, and a second guide (drilling guide) with holes 281 and 282 for performing the drilling. Because the adjustment block 100 and the pins in holes 282 provide common references, the holes 281 can still be drilled with proper location relative to the pin holes 282 and patterns 285, 286.

Figure 8:
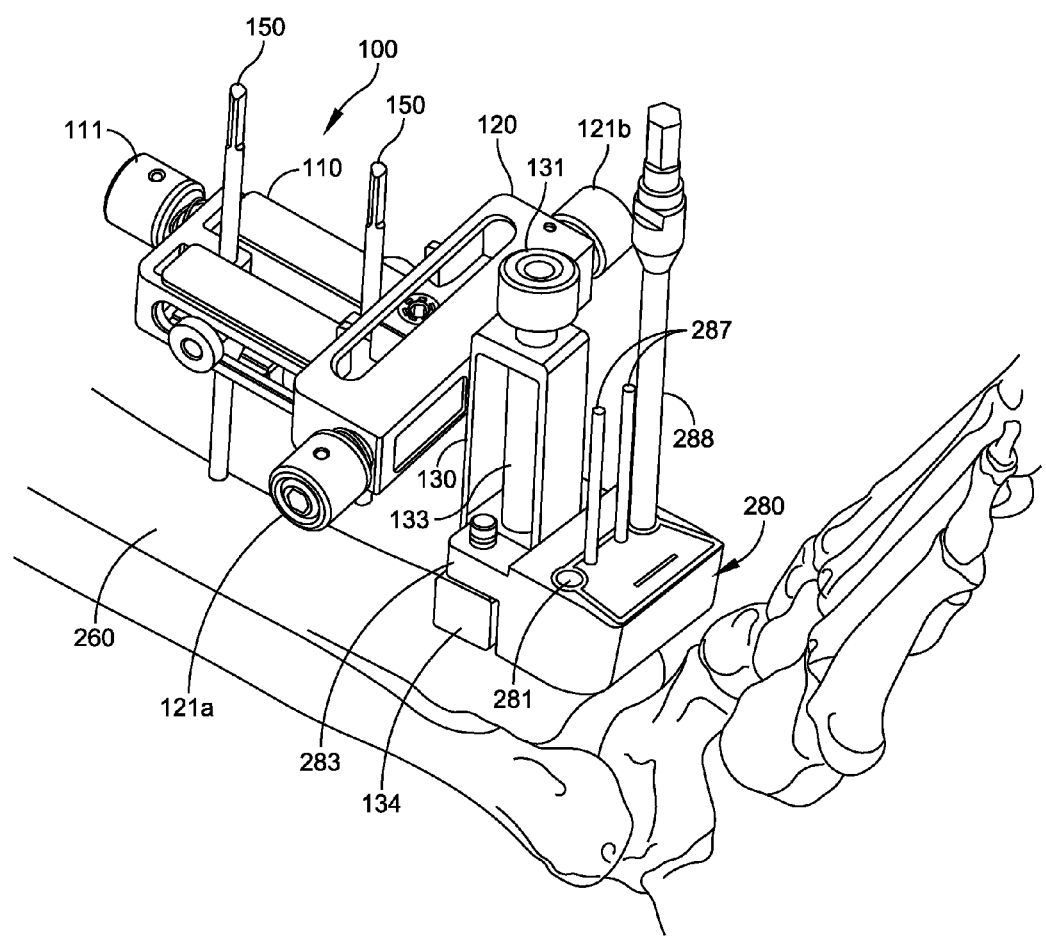
FIG. 8 is an isometric view of the adjustment block and drilling guide of FIG. 7, during the drilling operation.

FIG. 8 shows the tibia 260 with adjustment block 100 and drill guide 280. Soft tissue is omitted for ease of viewing. When the physician has verified that the optimum size of drill guide 280 has been selected, the physician pins the drill guide 280 to the tibia 260 using (e.g., 2.4 mm) fixation pins 287 inserted through the pin holes 282 and trimmed to extend slightly above the drill guide 280. Then the physician drills holes in the tibia 260 through the guides holes 281 using the drill guide 280 and drill 288. The holes thus drilled in the bone 260 define corners of a resectioning cut to be performed in the tibia. The physician then removes the drill guide 280, while leaving the pins 287 in place (in the distal portion of the tibia 260 to be removed by the resectioning). While removing the drill guide 280, the adjustment block can remain locked in the first coordinates with the first frame 110 adjusted to the same proximal-distal coordinate and the second frame 120 adjusted to the same medial-lateral coordinate.

Figure 9:
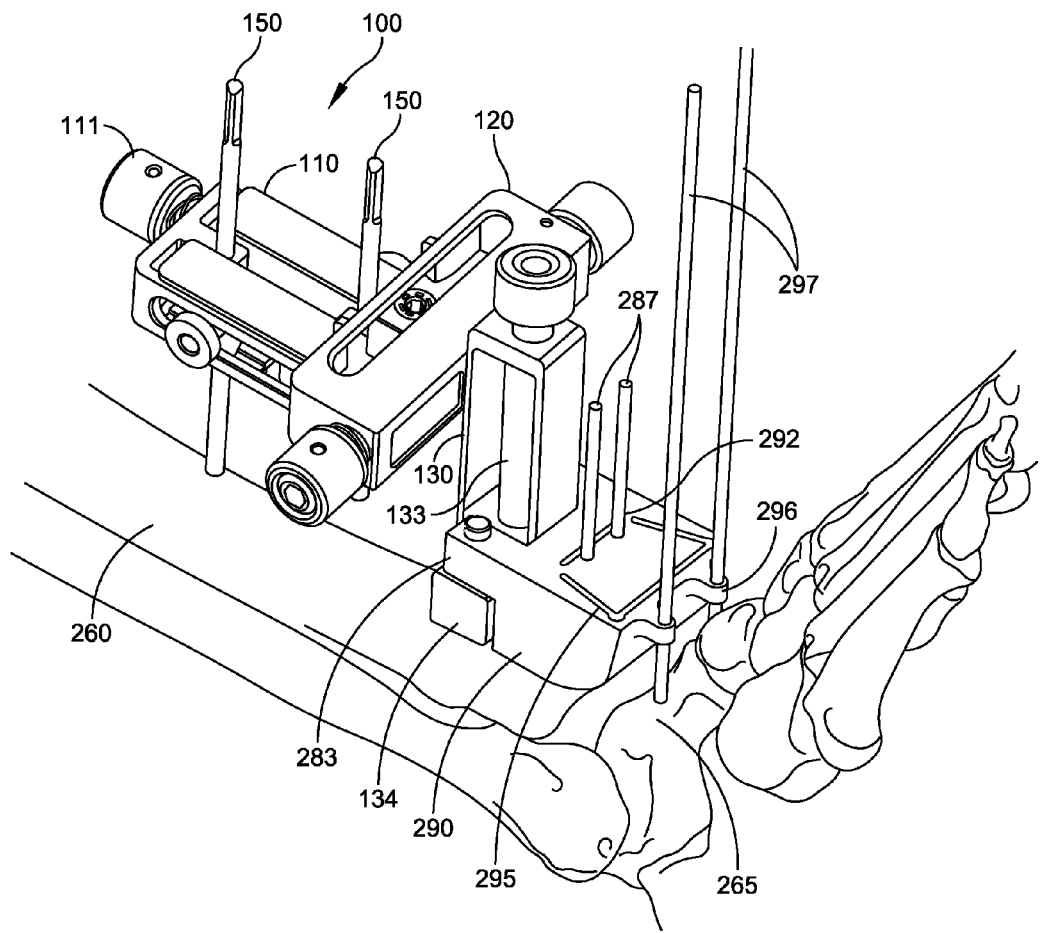
FIG. 9 is an isometric view of the adjustment block of FIG. 1, holding a cut guide.

FIG. 9 shows the adjustment block 100 still fixed to the fixation pins 150 in the same position, with a cut guide 290 mounted to the tool holder 134 of the adjustment block 100. The cut guide 290 has a plurality of slots 295, sized and located to connect the corner holes drilled with the drill guide 280. The cut guide 290 is sized and shaped to match the drill guide 280. Thus, the physician has a set of drill guides 280 and a corresponding set of cut guides 290. The selection of a drill guide size automatically selects the corresponding cut guide size to make cuts which are sized and located to connect the corner holes drilled with the drill guide 280, as described above. The cut guide 290 has a corresponding pair of mounting ears 293 with holes adapted to snap onto the pins 135. The cut guide 290 also has pin holes 292 which are sized and located to receive the fixation pins 287. This aligns the position of the cut guide 290 with the position previously occupied by the drill guide 280, to ensure alignment of the resectioning cuts with the previously drilled corner holes. In some embodiments, the cut guide 290 includes additional ears 296 with pin holes for receiving additional fixation pins 297.

To mount the cut guide 290, the physician slides the holes 292 of cut guide 290 over the fixation pins 287 and snaps the cut guide into place on the tool holder 134. For stability, the physician can then insert two more fixation pins 297 through the pin holes of ears 296 and into the talus bone 265. With the cut guide 290 and bones 260, 265 securely pinned, the physician performs the resectioning cuts through the guide slots 295, cutting the bone to connect the previously drilled holes. In some embodiments, as shown in FIG. 9, one cut guide 290 is used for both the tibia resection and the first cut of the talar resection. The cut guide 290 is then removed from the surgery site, and detached from the adjustment block 100. The sections of the tibia 260 and talus 265 that have been cut are removed, along with the fixation pins 287 and 297. In other embodiments (not shown), the tibia cut guide is only used to resection the tibia, and a separate cut guide is used to resection the talus after removal of the tibia cut guide.

The use of the adjustment block 100 permits the holes 281 to be drilled first with a first tool, and the cuts to be performed afterwards with a second tool, while maintaining accurate alignment between the holes and the cuts. Drilling the holes first avoids stress concentrations at the corners of the resectioned distal tibia.

Although some embodiments described herein use a drill guide 280 and a cut guide 290 commonly fixed using the adjustment block 100 and fixation pins 287, other embodiments attach different tools to the tool holder 134 for purpose of resectioning the tibia and talus. For example, some embodiments (not shown) include a cut guide without using a separate drill guide.

Following the initial resectioning, the physician inserts the tibia trial 210, poly trial insert 230 and floating trial 250, while the adjustment block 100 is still locked to the two fixation pins 150, and the tool holder 134 is in the first coordinates in the proximal-distal and medial-lateral directions. Should the physician choose to temporarily remove the adjustment block from the surgery site (e.g., for inspection, cleaning or suctioning), the physician returns the adjustment block to the same coordinates to locate the tool holder 134 at the same position to complete the procedure. Because the fixation pins 150 are excluded from the distal portion of the tibia removed by the resection, the fixation pins 150 are available throughout the procedure for use in adjusting or correcting the resection cuts.

Figure 10:
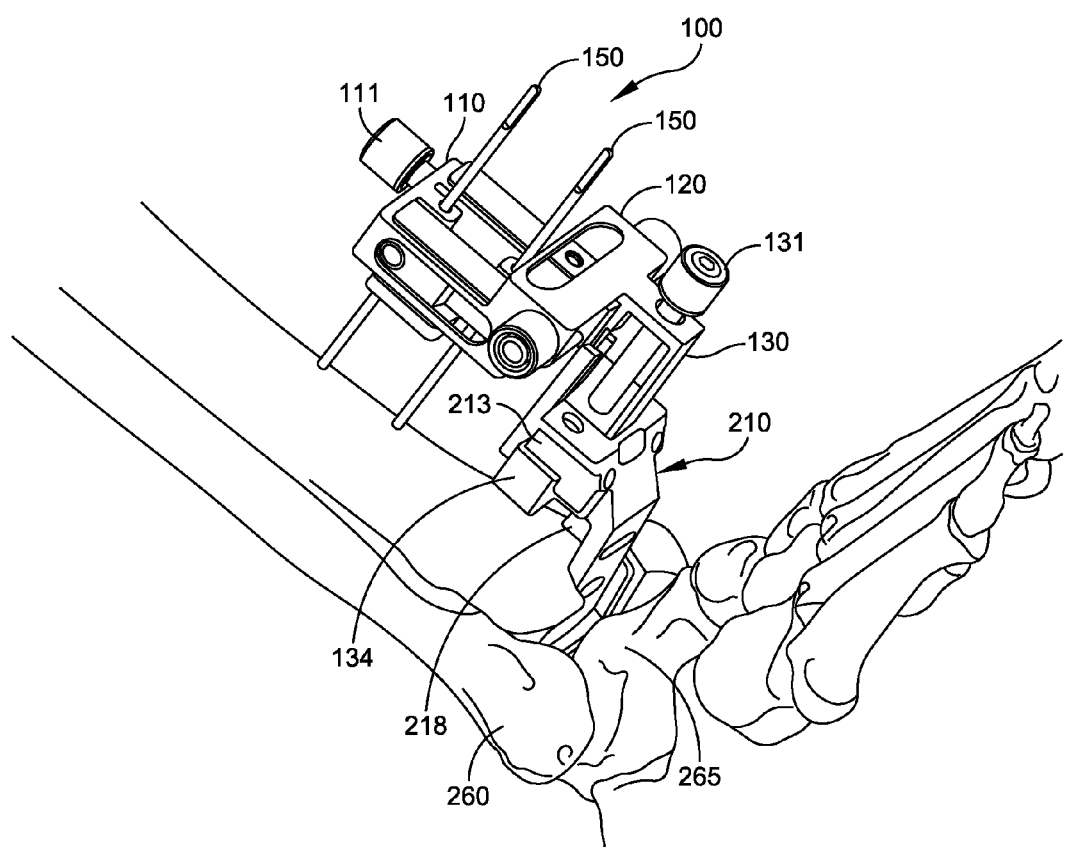
FIG. 10 is an isometric view showing the adjustment block and tibial trial during trial insertion.
Figure 11:
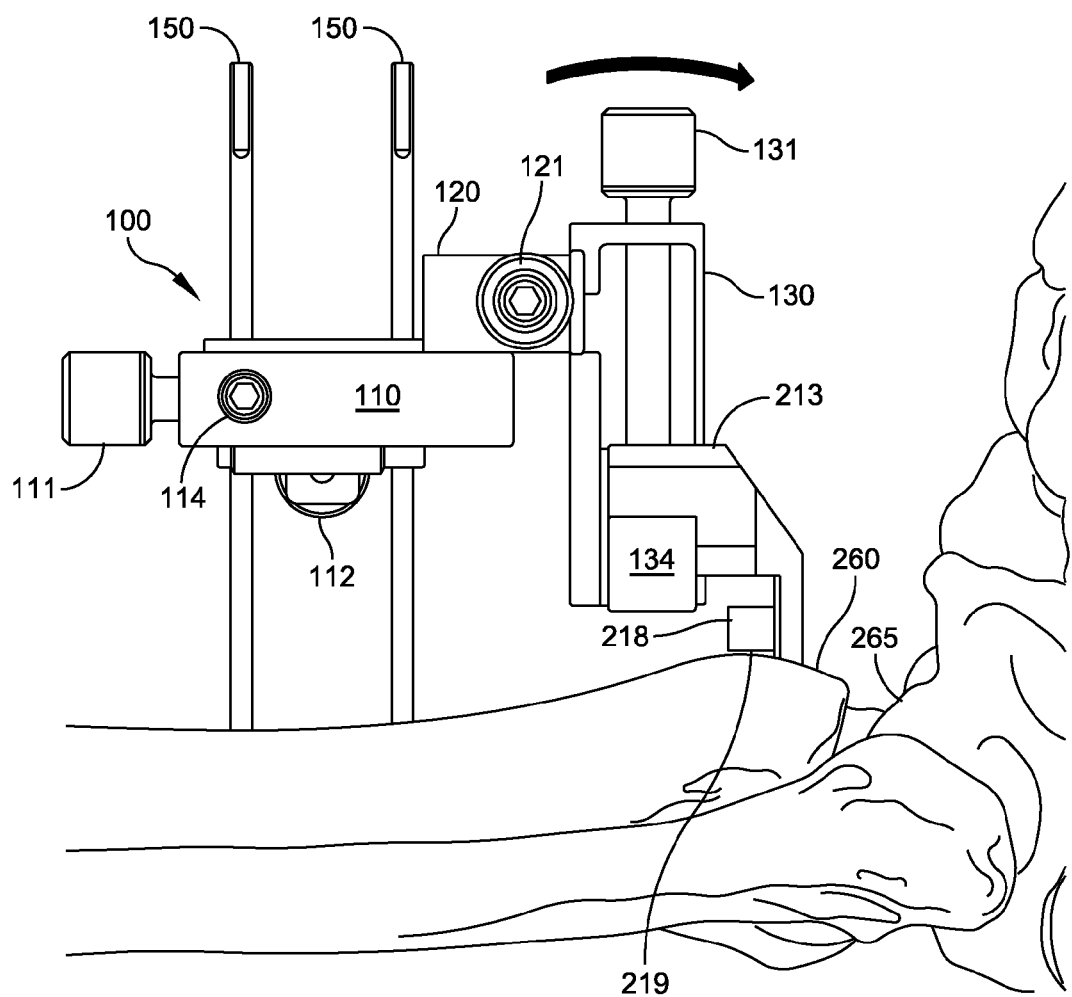
FIG. 11 is a lateral side elevation view of the adjustment block and tibial trial during trial insertion.

The physician snaps the tibia trial 210 onto the tool holder 134. FIGS. 10 and 11 show the adjustment block in position with the tibia trial 210 attached. The adjustment block 100 is adjusted to position the tool holder in an anterior-posterior direction, while the tool holder is at the first coordinates in the proximal-distal and medial-lateral directions. The tibia trial 210 is repositioned in the posterior direction until a predetermined portion of the tibia trail contacts an anterior cortex of the tibia. In some embodiments, the position of the third frame 130 is adjusted until the posterior surface 219 of anterior tibia reference member 218 extending from the plate 211 contacts the anterior cortex of the tibia 260.

Figure 12:
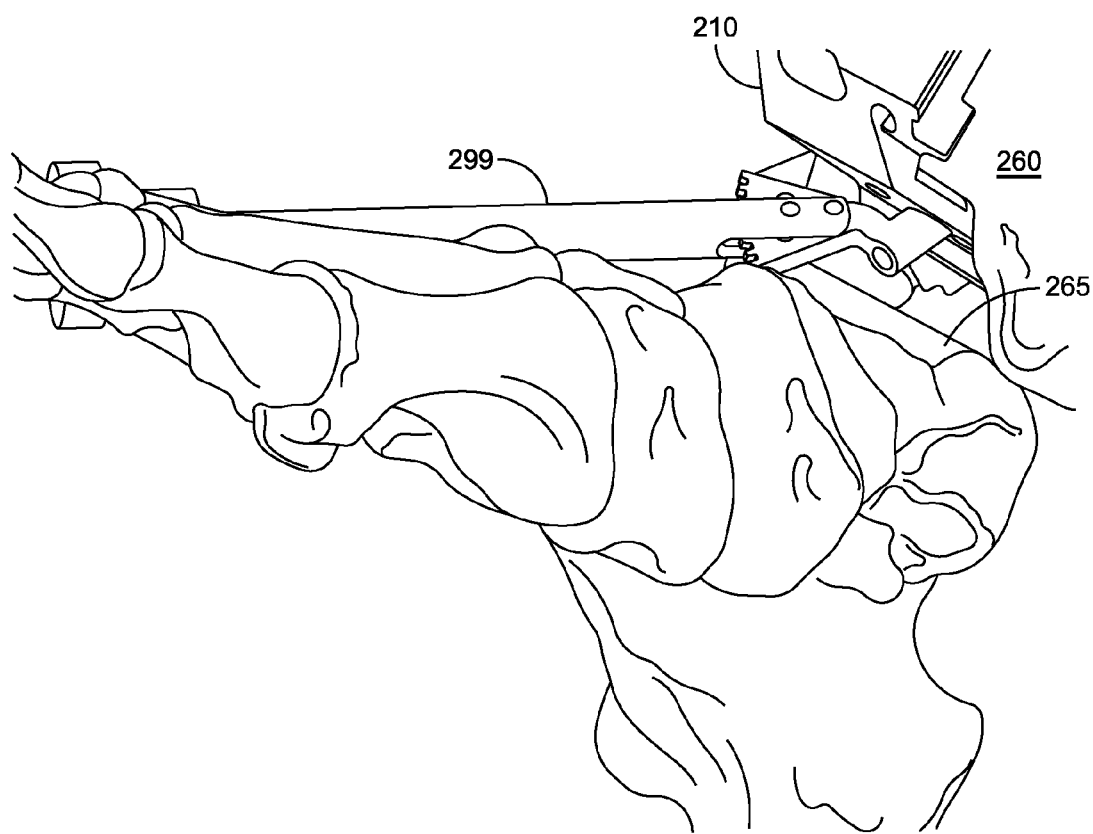
FIG. 12 is an isometric view showing drilling using the tibia trial to locate peg holes in the distal surface of the tibia.
Figure 13:
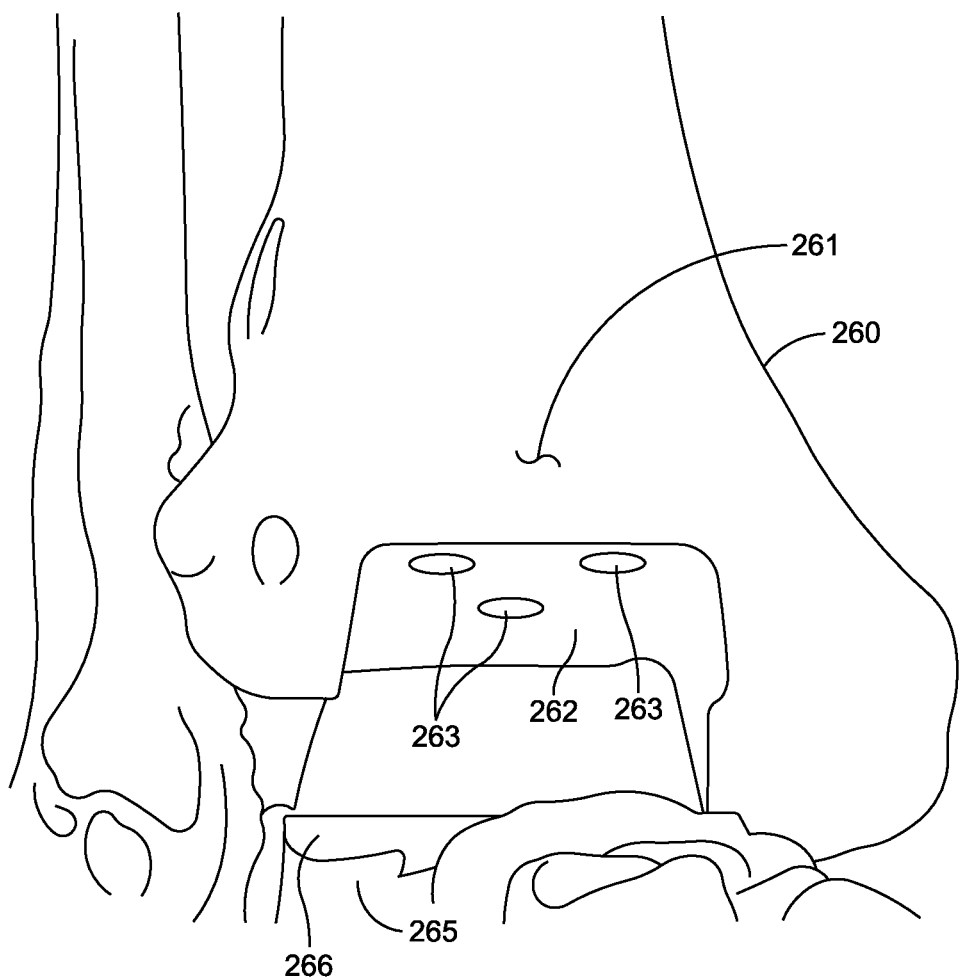
FIG. 13 shows the tibia and talus after resectioning.

FIG. 12 shows the tibia 260 and talus 265 with the adjustment block and tibia trial 210 in position. The tibia peg drill (not shown) is placed in the head of a tibia peg drill guide 299, and is inserted in the holes 212 (FIG. 3) of the tibia trial 210. The physician drills a plurality (e.g., 3) peg holes 263 in the distal surface 262 of the resectioned tibia 260 using the tibia peg drill 299. The holes 212 (FIG. 3) of the tibia trial 210 are used to locate these holes 263. FIG. 13 shows the distal end 261 of the tibia 260 at the completion of the peg drilling, with the three peg holes 263 in the resectioned surface 262 of the tibia.

The tibia trial 210 is used to verify size and shape of the resectioning using the tibia trial, prior to implanting the ankle replacement system. Advantageously, the steps of attaching the tibia trial 210 to the tool holder 134, adjusting the position adjustment device 100 to position the tool holder 134 in an anterior-posterior direction, and placing the tibia trial 210 on the resectioned tibia 260 using the tool holder 134, can be formed without inserting any additional location fixing pins into the tibia, while the tool holder is locked in the first coordinates in the proximal-distal and medial-lateral directions.

Figure 14:
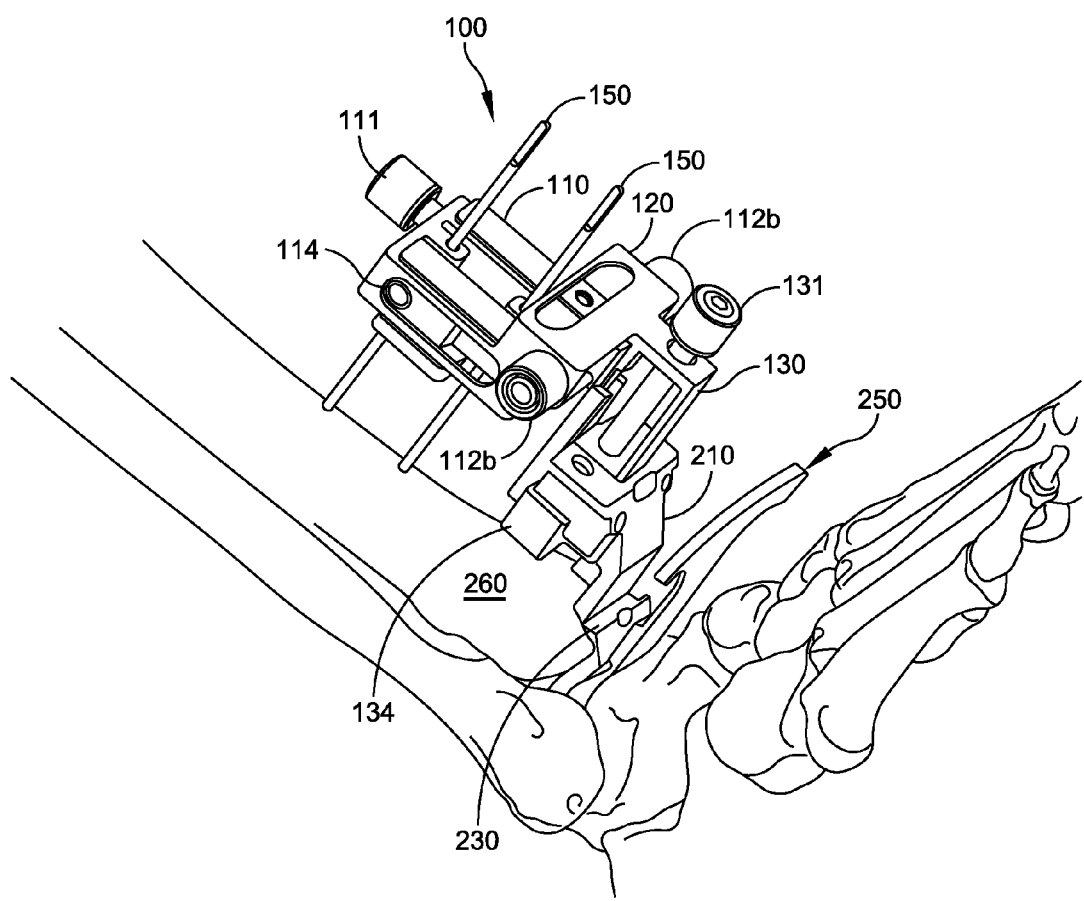
FIG. 14 is an isometric view showing the adjustment block, tibial trial, poly trial insert, and floating trial inserted in the surgical window.
Figure 15:
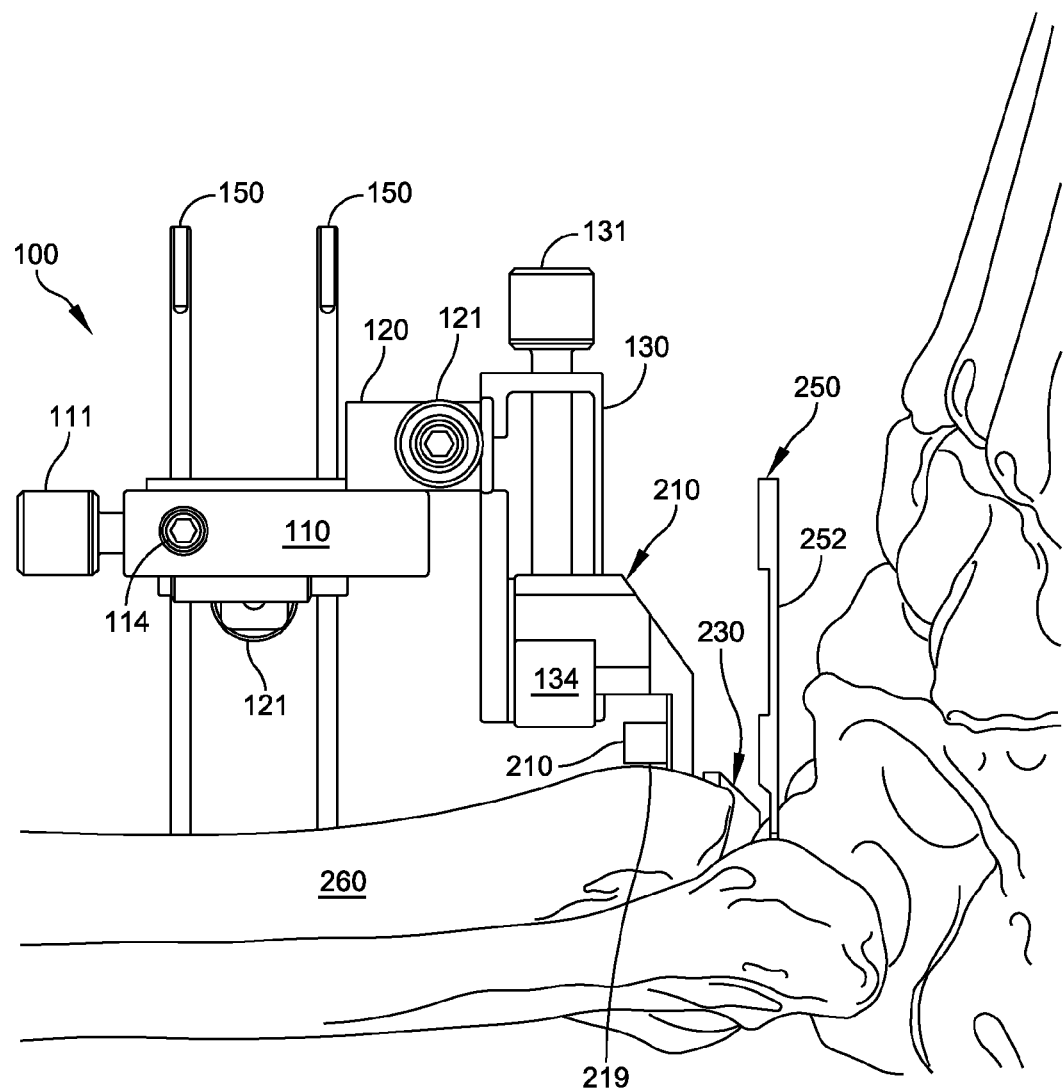
FIG. 15 is a lateral side elevation view of the adjustment block, tibial trial, poly trial insert, and floating trial inserted in the surgical window.

FIGS. 14 and 15 show the adjustment block 100 and tibia trial 210, after installing the poly trial insert 230 into the tibia trial 210 and positioning the floating trial 250 between the talus 265 and the poly insert trial 230, to permit articulation with the concave surface 232 of the poly insert trial 230 while the tool holder is in the first coordinates in the proximal-distal and medial-lateral directions. The physician can now assess the fit of the ankle replacement system, including size, anterior-posterior position, and whether the tibia has been sized, drilled and cut optimally. If any adjustments are deemed appropriate to the tibia resectioning, the physician can reapply the cut guide with the adjustment block set to the same proximal-distal and medial-lateral coordinates used before.

Figure 16:
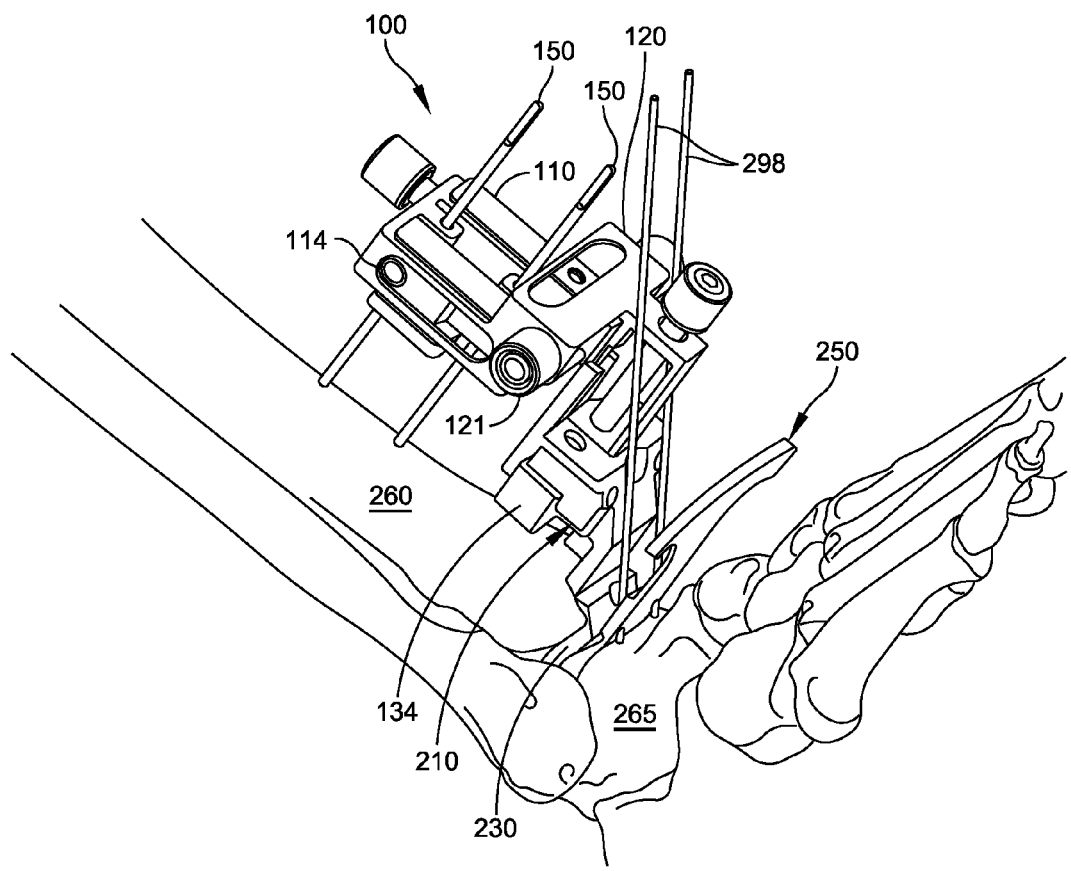
FIGS. 16 and 17 are isometric and lateral side elevation views showing the adjustment block, tibial trial, poly trial insert, and floating trial inserted while the floating trial is being pinned to the talus.
Figure 17:
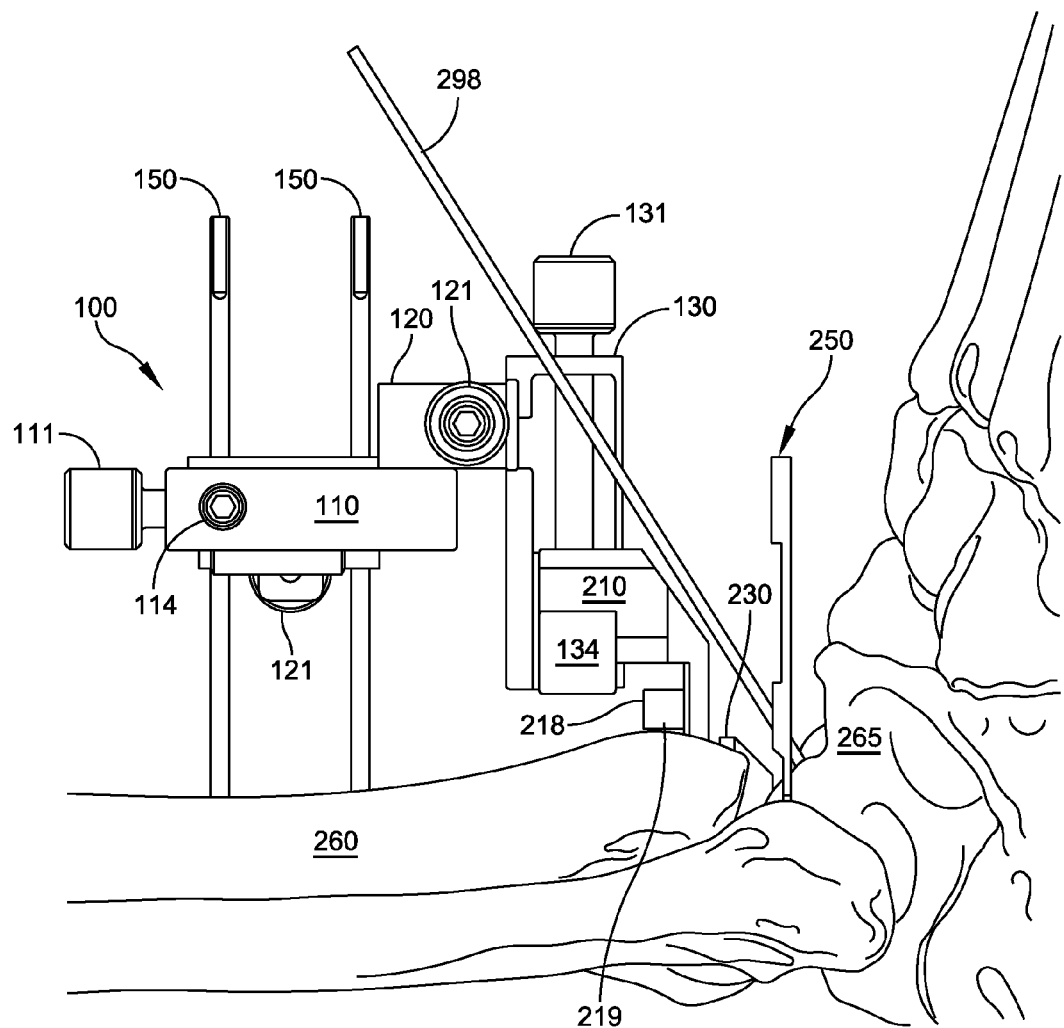

Referring to FIGS. 16 and 17, the physician now performs a trial reduction to ensure the correct poly insert height and talus dome position. The talar implant anterior-posterior coordinate is determined by moving the floating trial 250 to the location where it best articulates with the concave surface 232 of the poly trial insert 230. Two additional fixation pins 298 are inserted through the pin holes 253 of the floating trial 250 using 2 mm K-wire, for example. Additional resection guides (not shown) can be positioned by sliding pin holes in the resection guide(s) over the fixation pins 298. The remaining two talar cuts are then performed, to match the geometry of the talar dome implant of the ankle replacement system.

A position adjustment device (adjustment block) 100 as described above provides a fixed point of reference that facilitates the AP position of the tibial and talar implants of an ankle replacement system. The adjustment block 100 is capable of fixing a tibial trial 210 via a modular connection 134 to avoid insertion of additional pins in the distal tibia. The tibial trial 210, while attached to the adjustment block 100, allows the user to set the tibial implant anterior-posterior position by abutting the anterior post 218 against the tibial bone. The tibial trial 210 also serves as a drill guide to prepare the tibial pegs on the tibial implant.

The tibial trial 210 while rigidly fixed to the adjustment block 100 then translates the anterior-posterior position to the talar trial 250 by using the poly trial insert 230 to articulate with the talar (dome) trial 250. The talar trial 250 also has chamfer indicators 254 to help the user determine the optimal talar anterior-posterior position.

Advantageously, the system and method described above uses the adjustment block 100 as a fixed reference to associate all other instruments used for trial sizing and trials related to tibial side of the ankle replacement. Thus, a tibial sizer (e.g., drill guide 280), tibial resection guide (e.g., cut guide 290), and tibial trial 210 can all be anchored at the same position defined by the adjustment block 100. This method preserves the distal layer of the tibia to avoid excess pin holes from fixation pins and devices.

The compact size of the adjustment block allows the tools to be fixed and placed close to the surgery site, for more accurate cuts, with reduced chance of components flexing. Sizing guides (e.g., drill guide 280) and resection guides (e.g. cut guide 290) can all be placed in the surgical window. The position of the tools and trials can be accurately adjusted by turning the adjustment knobs 111, 121, 131 in a small area.

Figure 18:
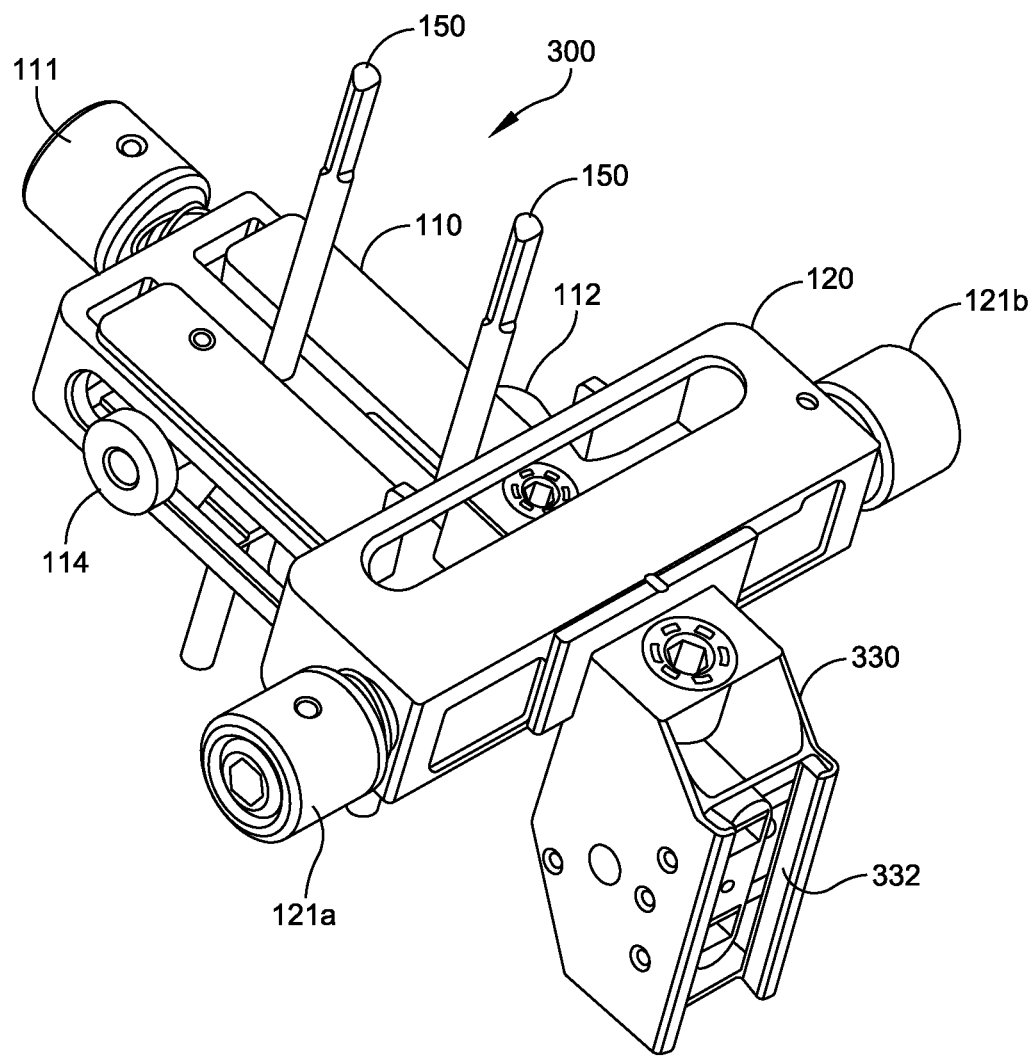
FIG. 18 is an isometric view of an embodiment of the adjustment block providing proximal-distal and medial-lateral adjustments.
Figure 19:
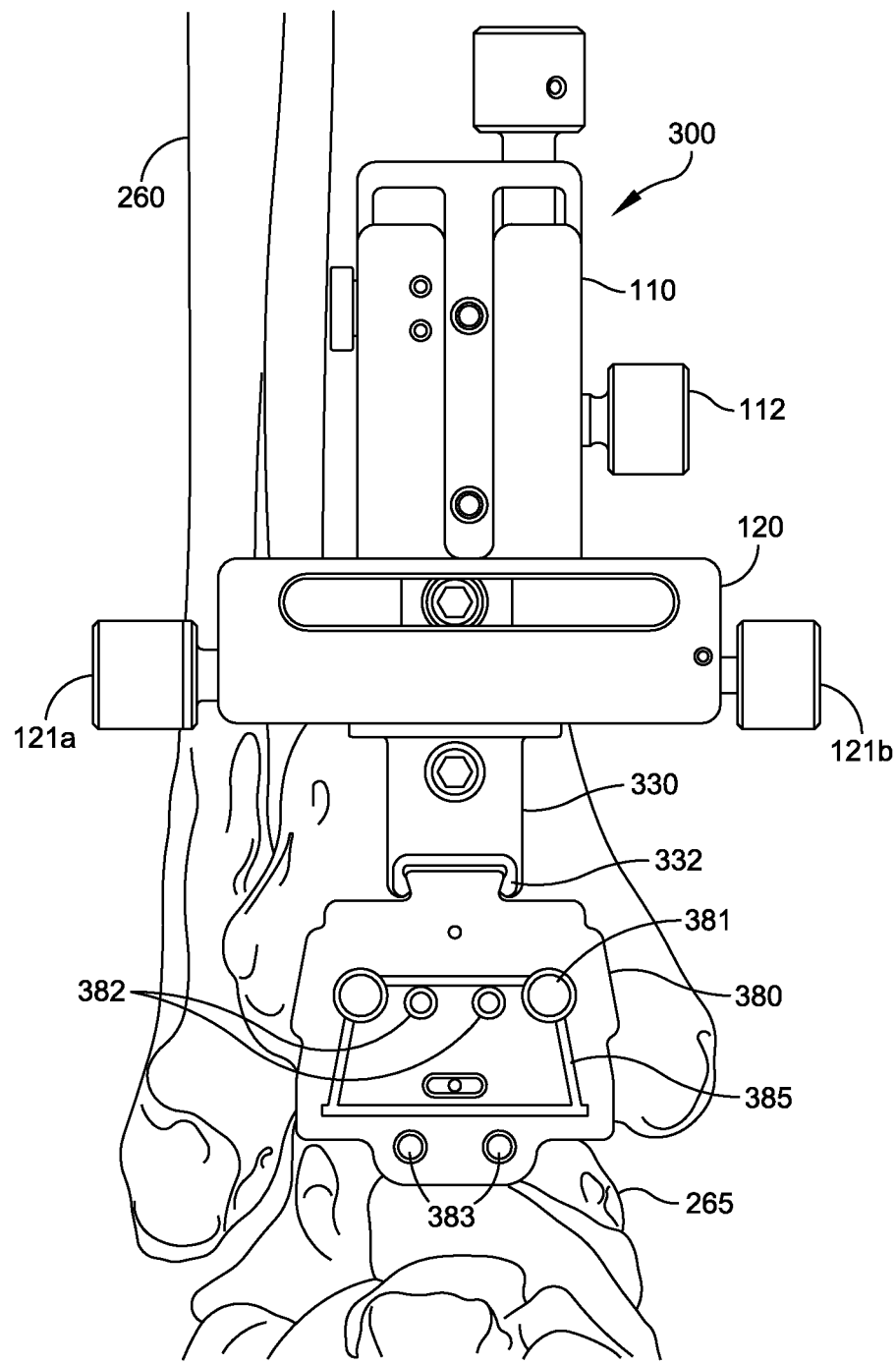
FIG. 19 is an anterior top plan view of the adjustment block of FIG. 18, with a drill guide attached to its tool holder.

FIGS. 18 and 19 show another embodiment of the adjustment block 300. The adjustment block 300 has two independently positionable frames 110, 120 for precisely positioning a tool holder 330 in the proximal-distal and medial-lateral directions, adjacent the joint to be replaced.

The first frame 110 is configured to be attached to two fixation pins 150 which have been inserted in the anterior surface of the tibia, near the distal end of the tibia. A locking screw 112 actuates a locking plate (not shown), which bears against the fixation pins 150 to secure the adjustment block 100 relative to the pins. The first frame has a proximal-distal adjustment knob 111 coaxially connected to a screw 113. The screw 113 can have an Acme thread, trapezoidal thread, square thread or other suitable thread for leadscrew use. The second frame 120 is fixedly attached or unitarily formed with a leadscrew nut (not shown), which the screw 113 drives. Rotation of the proximal-distal adjustment knob 111 rotates screw 113 to advance or retract the second frame 120 in the proximal-distal direction. When the second frame 120 is at the desired proximal-distal coordinate, the physician advances the locking screw 114 to lock the second frame 120 to the first frame 110 in place.

The second frame 120 has at least one medial-lateral adjustment knob 121a, 121b coaxially connected to a screw 123. The screw 123 can have an Acme thread, trapezoidal thread, square thread or other suitable thread for leadscrew use. The screw 123 drives a leadscrew nut (not shown), to which the tool holder 330 is fixedly attached or unitarily formed with. Rotation of the medial-lateral adjustment knob 121a or 121b rotates screw 123 to move the tool holder 330 in the medial-lateral direction. When the tool holder 330 is at the desired medial-lateral coordinate, the physician advances the locking screw 122 to lock the leadscrew 123 of the second frame 120 in place.

The position of the tool holder 330 in the anterior-posterior direction is determined by location of the first frame 110 relative to the pins 150.

The tool holder 330 can have any of a variety of configurations for easily attaching a tool or trial. FIGS. 18 and 19 show a non-limiting example in which the tool or trial is attached to the adjustment block 300 by a dovetail joint 332. FIG. 19 shows an example of a drill guide 380 adapted for mounting to the dovetail joint 332 of tool holder 330. The drill guide 380 has corner holes 381 and fixation holes 382, 383 and sizing patterns 385. Other tools (e.g., a cut guide) and trials (e.g., tibia trial) can be adapted to fit the tool holder 330.

Although the subject matter has been described in terms of exemplary embodiments, it is not limited thereto. Rather, the appended claims should be construed broadly, to include other variants and embodiments, which may be made by those skilled in the art.

What is claimed is:

1. Apparatus comprising:
   a position adjustment device having a tool holder, the position adjustment device being mountable to at least two pins projecting from respective anterior facing locations near a distal end of a tibia of a patient, the position adjustment device having first and second frames for adjusting a position of the tool holder in the proximal-distal and medial-lateral directions, the position adjustment device being lockable in the proximal-distal and medial-lateral directions, the tool holder configured for detachably mounting a first tool to the tool holder, the first tool configured for sizing a tibia implant, or for drilling or cutting a tibia bone; and
   a tibia trial detachably mountable on the tool holder, while the tool holder is in the first coordinates in the proximal-distal and medial-lateral directions, the tibia trial having a size and shape of a tibial tray of an ankle replacement system.

2. The apparatus of claim 1, wherein the tibia trial comprises:
   a plate having a top surface adapted to fit against a distal surface of a resectioned tibia, the plate having a plurality of holes to be used to locate peg holes in the resectioned tibia, the plate having a bottom surface adapted to receive an insert;
   an anterior tibia reference member extending from the plate, adapted to contact an anterior surface of the tibia when the tibia trial is properly positioned; and
   an anterior mounting portion sized and shaped to be mounted to the tool holder.

3. The apparatus of claim 2, further comprising the insert, wherein the insert comprises:
   a top surface adapted to be detachably mounted to the bottom surface of the plate of the tibia trial;
   a concave bottom surface with a size and shape of a prosthetic tibia joint surface of the ankle replacement system.

4. The apparatus of claim 3, further comprising a floating trial configured to contact the insert, the floating trial comprising:
   a member having at least one convex surface with a size and shape of a prosthetic talar dome of the ankle replacement system, to permit articulation with the concave surface of the insert,
   the member having a handle for manual positioning of the floating trial,
   the handle having a plurality of holes for inserting pins for locating a talar cut guide.

* * * * *